United States Patent [19]
Lindholm et al.

[11] Patent Number: 5,695,991
[45] Date of Patent: Dec. 9, 1997

[54] TARGETED DELIVERY OF VIRUS VECTOR TO MAMMALIAN CELLS

[75] Inventors: Leif Lindholm, Kullavik; Sven Enerbäck; Örjan Strannegård, both of Mölndal, all of Sweden

[73] Assignee: Got-A-Gene AB, Kullavak, Sweden

[21] Appl. No.: 232,028

[22] PCT Filed: Oct. 28, 1992

[86] PCT No.: PCT/SE92/00745

§ 371 Date: Jun. 17, 1994

§ 102(e) Date: Jun. 17, 1994

[87] PCT Pub. No.: WO93/09221

PCT Pub. Date: May 13, 1993

[30] Foreign Application Priority Data

Oct. 30, 1991 [SE] Sweden ............... 9103183

[51] Int. Cl.$^6$ ............... C12N 18/00; C07K 16/00; C07H 21/02; A01N 63/00
[52] U.S. Cl. ............... 435/320.1; 435/172.3; 530/387.1; 536/23.1; 424/93.2
[58] Field of Search ............... 424/93.2; 530/387.1; 435/172.3, 320.1; 536/23.1

[56] References Cited

U.S. PATENT DOCUMENTS 4,364,934  12/1982  Kung et al.
5,428,132  6/1995  Love et al. ............... 530/387.1

FOREIGN PATENT DOCUMENTS

| 2 649 119 | 6/1989 | France. |
|---|---|---|
| WO 89/07136 | 8/1989 | WIPO. |
| WO 90/12087 | 10/1990 | WIPO. |
| WO 91/02805 | 3/1991 | WIPO. |
| WO 91/04753 | 4/1991 | WIPO. |
| WO 92/06180 | 4/1992 | WIPO. |
| WO 93/09221 | 5/1993 | WIPO. |

OTHER PUBLICATIONS

Prowse et al., Immunochemistry, 1979, 15:429–436.
Schwartz, Annu. Rev. Immunol. 1990, 8:195–229.
Carlsson et al., Biochem. J. 1978, 173:723–737.
Koprowski, et al., Proc. Natl. Acad. Sci. USA, Jul., 1977, 7:2985–2988.
Roux et al., Proc. Natl. Acad. Sci. USA, Dec., 1989, 86:9079–9083.
McCafferty et al Valve 348: 552, 1990.
Love et al PNAS 84: 3896, 1987.

*Primary Examiner*—Suzanne E. Ziska
*Attorney, Agent, or Firm*—Pravel, Hewitt, Kimball & Krieger

[57] ABSTRACT

A complex between a virus the cell binding receptor of which has been inactivated and an antibody, said antibody having the ability to interact with a specific antigen on the surface of a mammalian cell different from the cellular structure which would otherwise mediate binding of the virus to the cell surface and which antigen has the ability to mediate entrance of a virus vector or infectious virus into mammalian cells.

**11 Cla

1. REPLACING ANTIBODY CONJUGATED TO BLOCKING ANTIBODY

VIRAL RECEPTOR     CELLULAR LIGAND

ANTIBODY AGAINST VIRAL RECEPTOR

VIRUS

CELL

ANTIBODY TO REPLACE VIRAL RECEPTOR

CELLULAR ANTIGEN

FIG. 1

2. REPLACING ANTIBODY CONJUGATED TO VIRUS

CELLULAR LIGAND

VIRUS

CELL

ANTIBODY TO REPLACE VIRAL RECEPTOR

CELLULAR ANTIGEN

FIG. 2

3. VIRAL GENE FOR RECEPTOR REPLACED WITH ANTIBODY GENES

TARGETED DELIVERY OF VIRUS VECTOR TO MAMMALIAN CELLS

The present invention relates to a complex between virus the cell binding receptor of which has been inactivated and an antibody. The invention is applicable to situations where it is desireable to introduce viruses into selected mammalian cells for medicinal purposes.

Viruses enter mammalian cells following binding between a viral receptor and a chemical structure, or ligand, in the cell membrane. This initial binding is a first and necessary step leading to the entry of virus into the cell and the subsequent transcription of the viral genome and replication of the virus within the cell. Rather detailed knowledge about the structure and specificity of many viral raceptors is at hand. For example, in the case of influenza virus the specificity of the virus receptor is analogous to the specificity of antibodies against certain tumor antigens, in that the influenza virus hemagglutinin binds to NeuAc2-3Gal-R, which is present on the same structures as many human tumor associated antigens.

The main object of the present invention is to provide techniques enabling introduction of viruses into mammalian cells for providing desired biological action in such cells.

Another object of the invention is to enable virus vectors or infectious viruses to be directed to specific cells in a living animal body.

Yet another purpose is to provide techniques making it possible for viruses to selectively enter specific cells in a living animal body.

For these and other purposes the invention provides for a complex between a virus and an antigen-binding substance selected from antibodies, fragments of antibodies and antigen-binding peptides, the cell binding receptor of said virus being inactivated. Said substance has the ability to interact with a specific antigen on the surface of a mammalian cell which antigen is different from the cellular structure which would otherwise mediate binding of the virus to the cell surface. Furthermore, said substance has the ability to mediate entrance of a virus vector or infectious virus into the cell.

The substance can either be a monoclonal antibody or a fragment of a whole antibody.

The substance can be bound to the virus in different ways, such as by chemical conjugation, by bridging the substance to the virus by an immunochemical reagent, or by using a bifunctional substance binding to the virus as well as to a cellular antigen.

The substance may also be expressed on the virus surface envelope following cloning into the virus genome of gene(s) for whole antibodies or fragments thereof.

The inactivation of the viral cell receptor in accordance with the present invention can take place by chemical means, by a specific antibody or by gene technological manipulation of the viral genome. Thus, the gene for the viral cell receptor or parts thereof can be replaced with antibody genes.

The complex according to the present invention is intended for medicinal use. Thus, the complex can be used as a vector to introduce genes into cells or organs for specific therapeutical purposes. The complex may also be used to express viral antigens on the cell surface for such purposes or it can be used to cause an infection in cells carrying the substance against which the antibody is reactive.

BRIEF DESCRIPTION OF THE FIGURES

FIG. 1 shows a schematic drawing of replacing antibody conjugated to blocking antibody;

FIG. 2 shows a schematic drawing of replacing antibody conjugated to virus;

FIG. 3 shows a schematic drawing of viral gene for receptor replaced with antibody genes; and FIG. 4 shows a schematic representation of the use of an antibody conjugate of the present invention.

By using an antibody which binds to a cellular membrane antigen which can be internalized into the cell, virus can bind to the cell via an antibody-antigen reaction and then penetrate into the cell and replicate causing a viral infection. Furthermore, since antigens are known which are more or less unique for certain types of cells, virus can be selectively directed to enter and infect specific cells in the body. Examples of such antigens are some cell-differentiation antigens, such as CD19 on B cells, and certain tumor-associated antigens on carcinoma cells.

The invention will therefore make it possible to direct virus vectors or infectious viruses to specific cells in the body with the possibility of introducing functional genes into selected cells or organs in vivo or to cause a viral infection in certain cells.

The following table shows examples of viral receptors and their cellular ligands. Receptors such as these are possible candidates for use within the present invention.

TABLE 1

Some viral receptors and their cellular ligands.

| Virus | Cellular ligand | Distribution | Viral receptor |
| --- | --- | --- | --- |
| Epstein-Barr | CD21 | B cells | gp350/220 |
| Influenza A | Sialyloglycolipid or Sialyloglycoprotein containing NeuAc2-3Gal-R | Many cell types | Hemagglutinin |
| Paramyxovirus prot | Sialic acid-containing carbohydtrates | Many cell types | HN, H and G |
| Retrovirus | Protein | Many cell types | SU protein |

When virus replicates in the cell certain viral proteins are degraded to peptides. These peptides are bound to so called MHC antigens within the cell and are thereafter transported to the cell membrane where the peptide-MHC complex serves as target for a very important defense system, i.e. virus specific cytotoxic T cells, which actually kill the viruses infected cell. Certain virus, e.g. retroviruses, are integrated into the host cell genome in the form of a provirus which may thereafter be replicated. By "genetic engineering" methods retroviruses can be manipulated so that they no longer replicate but can be used as vectors to introduce new genes into mammalian cells. The use of retroviral vectors offers a practical means for gene therapy in humans. However, at the present time the use of retroviral vectors are largely restricted to cells of hemopoietic origin.

There are several technical ways which the cell-binding receptor of a virus can be replaced with an antibody. Some principal ways are listed below and illustrated in the appended drawings, viz. FIGS. 1 to 3.

1. The viral receptor can be blocked with an antibody which may in turn be conjugated with an antibody of the desired specificity (a bifunctional antibody).

2. The viral receptor can be inactivated by chemical- or gene technological methods and the replacing antibody can then be chemically coupled directly to the virus particle.

3. The gene for the viral receptor can be replaced with the genes for the replacing antibody.

The possibilities inherent in this invention are many. One area is gene therapy in humans where retroviral vectors have already been used to introduce genes into human cells for therapeutic purposes. The present invention may be expected to increase the efficiency of this approach as well as making possible new areas of use, such as the deliberate introduction of genes into tumor cells.

Another area is immunotherapy of tumor diseases where the invention might be used for gene therapy or to introduce virus into tumor cells with the intent of expressing viral antigens at the cell surface converting the cells into possible targets for the virus-specific cytotoxic T cells.

The invention will be further illustrated in the following by specific examples which are not construed to restrict the scope of the invention otherwise than defined by the appended claims.

EXAMPLE 1

The following examples demonstrate that the binding specificity of a virus can be blocked and replaced with that of an antibody. In the examples the binding and infection of Influenza virus A/PR/8 to human colon carcinoma cells Colo 205 is used. The cell binding of influenza virus is dependant on a specific binding molecule, Hemagglutinin (HA), which is present in the viral envelope, and which binds to NeuAc2-3Gal-R, present on many mammalian cells.

In this example the following strategy was employed.

1. The binding of A/PR/8 to the target cell was blocked by means of the monoclonal antibody HK-PEG-1 against influenza HA (Koprowski H, Gerhard W and Croce CM: Production of antibodies against influenza virus by somatic cell hybrids between mouse myeloma and primed spleen cells. Proc. Natl.Acad. Sci USA, Vol. 74, pp 2985–2988, 1977). The cell line producing this antibody is obtainable from the American Type Culture Collection, 12301 Parklawn Drive, Rockville, Md. 20852, USA.

2. A new binding specificity was conferred on the virus by another antibody which had been chemically conjugated to the HK-PEG-1 antibody used to block the natural cell binding of the virus. The antibody OKT9 (U.S. Pat. No. 4,364,934) which reacts with the transferrin receptor on proliferating mammalian cells was used for this purpose. An antibody against the transferrin receptor was used because the transferrin receptor is rapidly and constitutively internalized by the cells along with an antibody which has been reacted with the receptor (Schwartz AL: Cell Biology of Intracellular Protein Trafficking, Ann. Rev. Immunol., Vol 8, pp 195–229, 1990). The cell line producing the OKT9 antibody is obtainable from the American Type Culture Collection.

The expected duel effect on virus binding of the antibody conjugate used is schematically shown in FIG. 4 of the drawings.

EXAMPLE 2

Influenze A/PR/8 was obtained from Statens Bakteriologiska Leboratorium, S-10521 Stockholm, Sweden.

HK-PEG-1 end OKT9 antibody

Hybridoma cells were obtained from the American Type Culture Collection, 12301 Parklawn Drive, Rockville, Md. 20852, USA. Hybridoma cells were grown in Iscove's medium supplemented with 10% fetel calf serum. Antibody production was performed in dialysis tubings (Sjögren-Jansson E and Jeansson S: Large-Scale Production of Monoclonal Antibodies in Dialysis Tubin, J.Immunol.Meth., Vol 84, pp 359–364, 1985) and antibodies were purified by affinity chromatography on a Protein A Sepherose CL-4B (Pharmacia, Uppsala, Sweden)(Ey PL, Prowse SJ and Jenkin CR: Isolation of pure IgG1, $IgG_{2a}$ and $IgG_{2b}$ immunoglobulins from mouse serum using Protein A-Sepharose. Immunochemistry Vol 15, pp 429–436, 1978).

Antibody conjugates:

Antibody conjugates were prepared using the heterobifunctional reagent N-succinimidyl (2 pyridyldithio) propionate, SPDP (Pharmacia, Uppsala, Sweden) (Carlsson J, Drevin H end Axén R: Protein thiolation and reversible protein protein conjugation. N-succinimidyl 3(2 pyridyldithio)propionate —a new heterobifunctional reagent. Biochem. J., Vol 173, pp 723–737, 1978). Conjugates were purified from unreacted antibody by gel filtration on Superdex 200 (Pharmecia, Uppsala, Sweden).

Titration of virus by Hemagglutination:

Hemagglutination of human blood group O red blood cells was performed in 96-well trays using standard methods (Mahy BWJ, ed: Virology, a practical approach. IRL Press, Oxford, 1985).

Colo 205 colon carcinoma cells were obtained from the American Type Culture Collection, 12301 Parklawn Drive, Rockville, Md. 20852, USA, and maintained in Iscove's medium with 10% fetal calf serum.

Results

Inhibition of viral binding by HK-PEG-1 antibody and HK-PEG-1 conjugates.

Inhibition of viral binding to its cellular ligand was measured by the hemagglutination method. Virus, 800 HAU (HemAgglutinating Units)/ml, was incubated for 1 h at room temperature with antibody at different concentrations and then allowed to agglutinate human red blood cells. HK-PEG-1 antibody caused complete inhibition of agglutination at 7 µg/ml or more whereas the corresponding figure for HK-PEG-1 conjugated to OKT9 was 10 µg/ml.

Ability of HK-PEG-1 conjugates to mediate viral infection.

HK-PEG-1 or HK-PEG-1 conjugated to OKT9 was incubated with 100 HAU of A/PR/8 virus for 1 hour at room temperature in order to block the HA molecules in the viral envelope. Thereafter the virus preparations were incubated together with $2 \times 10^6$ Colo 205 cells in 1 ml PBS for 1 hour at 37°. The cells were washed three times with PBS by centrifugation, suspended in 1 ml of complete medium and incubated at 37° for 24 hours. Presence of virus in the medium was assessed by hemagglutination. The results are shown in Table 2 below. It is evident that the conjugation of OKT9 to HK-PEG-1 allows the virus to infect the cells by giving the virus a new binding site in the cell membrane, thereby overcoming the inhibition caused by the HK-PEG-1 antibody alone. The decreasing infectivity with increasing antibody concentration is probably an effect of formation of large virus-antibody complexes since such complexes are less effectively taken up into the cell.

TABLE 2

Production of virus as measured by hemagglutination by Colo 205 cells infected with Influenza A/PR/8 pretreated with different antibodies.

| Antibody | Concentration (μg/ml) | HA-titer |
|---|---|---|
| None | | 1/16 |
| HK-PEG-1 | 30 | Negative (<1/2) |
| HK-PEG-1 | 100 | Negative (<1/2) |
| HK-PEG-1 | 300 | Negative (<1/2) |
| HK-PEG-1/OKT9 | 30 | 1/8 |
| HK-PEG-1/OKT9 | 100 | 1/4 |
| HK-PEG-1/OKT9 | 300 | 1/2 |

What is claimed is:

1. A complex comprising:

a virus, the cell binding receptor of which has been inactivated; and an antigen-binding substance selected from antibodies, fragments of antibodies and antigen-binding peptides, said antigen-binding substance having the ability to bind a specific cell surface antigen which specific cell surface antigen differs from specific antigens which normally mediate binding of the virus to the cell surface and which specific cell surface antigen mediates entrance of the virus into said specific cells.

2. The complex of claim 1, wherein the antigen-binding substance is a monoclonal antibody.

3. The complex of claim 1, wherein the antigen-binding substance is a fragment of a whole antibody, said fragment being prepared by chemical means or by expression of antibody genes or DNA sequences derived from said genes.

4. The complex of claim 1, wherein the antigen-binding substance is an antigen-binding peptide.

5. The complex of claim 1, wherein the antigen-binding substance is bound to the virus by chemical conjugation.

6. The complex of claim 1, wherein the antigen-binding substance is bridged to the virus by an immunochemical reagent, selected from the group consisting of an anti-species antibody, avidin or streptavidin.

7. The complex of claim 1, wherein the antigen-binding substance is a bifunctional antibody which binds to a virus as well as to a cellular antigen.

8. The complex of claim 1, wherein said virus has been genetically altered to include DNA sequences coding for antibodies or antibody binding structures.

9. The complex of claim 1, wherein the antigen-binding substance is reactive with a cellular antigen capable of mediating entry of the virus into a cell.

10. The complex of claim 1, wherein the cell linking receptor has been inactivated by chemical means, by a specific antigen, or by manipulation of the viral genome.

11. The complex of claim 1, wherein the viral gene for the cell linking receptor or parts thereof has been replaced with a gene encoding an antibody.

* * * * *